tion in a solid unit dosage form for oral administration in a human or lower animal comprising: a. a safe and effective amount of a therapeutically active agent; b. an inner coating layer selected from the group consisting of poly(methacrylic acid, methyl methacrylate) 1:2, poly(methacrylic acid, methyl methacrylate) 1:1, and mixtures thereof; and c. an outer coating layer comprising an enteric polymer or film coating material; wherein the inner coating layer is not the same as the outer coating layer; wherein if the inner coating layer is poly(methacrylic acid, methyl methacrylate) 1:1 then the outer coating layer is not poly(methacrylic acid, methyl methacrylate) 1:2 or is not a mixture of poly (methacrylic acid, methyl methacrylate) 1:1 and poly (methacrylic acid, methyl methacrylate) 1:2; and wherein the inner coating layer and the outer coating layer do not contain any therapeutically active agent. This invention further relates to a method of maintaining the desired site of delivery of a therapeutic agent in the gastrointestinal tract by administering the above compositions to a human or lower animal.

(12) United States Patent
Dittmar et al.

(10) Patent No.: US 6,893,662 B2
(45) Date of Patent: May 17, 2005

(54) PHARMACEUTICAL DOSAGE FORM WITH MULTIPLE COATINGS FOR REDUCED IMPACT OF COATING FRACTURES

(75) Inventors: Gregory Paul Dittmar, Norwich, NY (US); Joseph Michael Amante, Norwich, NY (US); Tony Ryan Cronk, Mishawaka, IN (US); Daniel Gary Newby, New Berlin, NY (US)

(73) Assignee: The Procter & Gamble Company, Cincinnati, OH (US)

(*) Notice: Subject to any disclaimer, the term of this patent is extended or adjusted under 35 U.S.C. 154(b) by 0 days.

(21) Appl. No.: 09/996,555

(22) Filed: Nov. 15, 2001

(65) Prior Publication Data

US 2002/0098235 A1 Jul. 25, 2002

Related U.S. Application Data

(60) Provisional application No. 60/252,122, filed on Nov. 20, 2000.

(51) Int. Cl.$^7$ ............................. A61K 9/24; A61K 9/28; A61K 9/36; A61K 9/32; A61K 9/14
(52) U.S. Cl. ....................... 424/472; 424/474; 424/484; 424/479; 424/464; 424/480; 424/482; 424/486; 424/487; 424/470; 424/476; 424/489
(58) Field of Search .................................. 424/484, 479, 424/464, 480, 482, 470, 476, 474, 486, 487, 472, 489, 468

(56) References Cited

U.S. PATENT DOCUMENTS

| | | | |
|---|---|---|---|
| 4,312,806 A | | 1/1982 | Lambert et al. |
| 4,432,966 A | | 2/1984 | Zeitoun et al. |
| 4,678,516 A | | 7/1987 | Alderman et al. |
| 4,780,318 A | | 10/1988 | Appelgren et al. |
| 4,888,179 A | | 12/1989 | Appelgren et al. |
| 4,910,021 A | | 3/1990 | Davis et al. |
| 5,171,580 A | * | 12/1992 | Iamartino et al. ........... 424/490 |
| 5,175,003 A | | 12/1992 | Goldman |
| 5,186,943 A | | 2/1993 | Okada et al. |
| 5,217,720 A | | 6/1993 | Sekigawa et al. |
| 5,270,055 A | | 12/1993 | Moest et al. |
| 5,316,772 A | | 5/1994 | Jurgens, Jr. et al. |
| 5,342,627 A | | 8/1994 | Chopra et al. |
| 5,476,667 A | | 12/1995 | Kristensen et al. |
| 5,482,718 A | * | 1/1996 | Shah et al. .................. 424/480 |
| 5,500,227 A | | 3/1996 | Oshlack et al. |
| 5,519,014 A | | 5/1996 | Borody |
| 5,536,507 A | | 7/1996 | Abramowitz et al. |
| 5,540,945 A | | 7/1996 | Ikushima |
| 5,580,578 A | | 12/1996 | Oshlack et al. |
| 5,639,476 A | | 6/1997 | Oshlack et al. |
| 5,654,004 A | | 8/1997 | Okayama et al. |
| 5,656,290 A | | 8/1997 | Kelm et al. |
| 5,686,105 A | | 11/1997 | Kelm et al. |
| 5,686,106 A | | 11/1997 | Kelm et al. |
| 5,716,648 A | | 2/1998 | Halskov et al. |
| 5,788,987 A | | 8/1998 | Busetti et al. |
| 5,837,277 A | | 11/1998 | Hayward |
| 5,895,663 A | | 4/1999 | Irwin et al. |
| 5,900,252 A | | 5/1999 | Calanchi et al. |

FOREIGN PATENT DOCUMENTS

| | | |
|---|---|---|
| EP | 0 040 590 | 11/1981 |
| EP | 0 225 189 | 6/1987 |
| WO | WO 98 27967 A | 7/1998 |
| WO | WO 98/27967 * | 7/1998 |
| WO | WO 00/28974 | 5/2000 |

OTHER PUBLICATIONS

Handbook of Pharmaceutical Excipinets, 2$^{nd}$ ed., Wade et al. edidted, pp. 362–363.*
M. Zahirul I. Khan, et al; A pH–Dependent Colon–Targeted Oral Drug Delivery System Using Methacrylic Acid Copolymers. II. Manipulation of drug Release Using Eudragit® L100 and Eudragit S100 Combinations, Drug Develop Ind Pharmacy 26(5): 549–554 May 2000.
M. Zahirul I. Khan, et al; A pH–dependent colon targeted oral drug delivery system using Methacrylic acid copolymers I. Manipulation of drug release using Eudragit® L100–55 and Eudragit® S100 combinations, J. Controlled Release 58(2): 215–222 (Mar. 29, 1999), 1999 Elsevier Science B.V..
M. Zahirul I. Khan, et al; A pH–Dependent Colon Targeted Oral Drug Delivery System Using Methacrylic Acid Copolymers. II. Manipulation of Drug Release Using Eudragit® L100 and Eudragit® S100 Combinations, Drug Development and Industrial Pharmacy, 26(5), pg 549–554 (2000).
Jordan et al., "A Comparision of the Performance Characteristics of Enteric Film Coating Systems", *Technical Data—Colorcon*, Poster reprint from AAPS Meeting, 1999, pp. 1–5.

* cited by examiner

Primary Examiner—Thurman K. Page
Assistant Examiner—Blessing Fubara
(74) Attorney, Agent, or Firm—Andrew A. Paul; David V. Upite; Mary Pat McMahon

(57) ABSTRACT

The present invention relates to a pharmaceutical composi-

35 Claims, No Drawings

PHARMACEUTICAL DOSAGE FORM WITH MULTIPLE COATINGS FOR REDUCED IMPACT OF COATING FRACTURES

CROSS REFERENCE TO RELATED APPLICATION

This application claims the benefit of U.S. Provisional Application No. 60/252,122, filed Nov. 20, 2000.

TECHNICAL FIELD

The present invention relates to novel unit dosage forms comprising therapeutic agents with improved resistance to coating fractures during processing, manufacturing or packaging.

BACKGROUND OF THE INVENTION

A number of prior art references teaches the advantages of delivery of therapeutic agents to the lower part of the gastrointestinal tract, especially the large intestine or the colon. These reference illustrate the difficulty of formulating dosage forms that will achieve this delivery benefit. For example, U.S. Pat. Nos. 5,541,170 and 5,541,171, Rhodes et al., both issued Jul. 30, 1996, discuss the delivery of pharmacologically active agents, especially 5-aminosalicylic acid, to the large intestine for the treatment of colonic or rectal disorders. U.S. Pat. No. 5,686,105, Kelm et al., issued Nov. 11, 1997, teaches colonic delivery of therapeutic agents wherein the dosage form comprises a coating system with at least one inner coating layer and one outer coating layer. The inner coating layer is an enteric polymer that begins to dissolve in an aqueous media at a pH between about 5 to about 6.3, and the outer coating layer is an enteric polymer that begins to dissolve in an aqueous media at a pH of between about 6.8 to 7.2. U.S. Pat. No. 5,171,580, Iamartino et al., issued Dec. 15, 1992, teaches pharmaceutical preparations containing an active ingredient to be released in the lower part of the gastrointestinal tract, the large intestine and especially the colon, consisting of a core with the active, the core being coated with three protective layers at different solubilities. This reference focuses on providing more specific and reliable release of a therapeutic active agent to the lower part of the gastrointestinal tract, especially the colon, achieved with the three protection layers, as well as the benefits of having a selective effect in the colon. Other prior art references also focus on the benefits of delivering therapeutic agents to the colon. These references include U.S. Pat. Nos. 5,686,106, Kelm et al., issued Nov. 11, 1997; U.S. Pat. No. 5,914,132, Kelm et al, issued Jun. 22, 1999; U.S. Pat. No. 4,910,021, Davis et al, issued Mar. 20, 1990; U.S. Pat. No. 4,432,966, Zeitoun et al., issued Feb. 21, 1984; U.S. Pat. No. 5,654,004, Okayama et al., issued Aug. 5, 1997; U.S. Pat. No. 5,900,252, Calcanchi et al., issued May 4, 1999; U.S. Pat. No. 5,482,718, Shah et al, issued Jan. 9, 1996; U.S. Pat. No. 5,316,772, Jurgens et al., issued May 31, 1994; EP 225,189, Davies, et al, published Jun. 10, 1987; and Khan et al., *Drug Development and Industrial Pharmacy*, 26(5), 549–554 (2000).

None of the above prior art references, however, discusses the problem or possibility of coating fractures that may occur during processing, manufacturing, or packaging of the oral unit dosage form. Coating fractures may cause unreliable or inconsistent delivery or release of the therapeutic agent to the desired region of the gastrointestinal tract. These fractures may be associated with premature rupture or release of the unit dosage forms. Indeed, coating fractures may especially be problematic for larger than average size unit dosage forms or heavier unit dosage forms resulting from using larger dosages/levels of the therapeutic active.

The present invention, therefore, relates to solid unit dosage forms for oral administration in humans or lower animals which minimizes the impact or negative effects of coating fractures, especially for larger or heavier unit dosage forms. By reducing these negative effects, these compositions maintain the desired site of delivery of the therapeutic agents in the gastrointestinal tract.

SUMMARY OF THE INVENTION

The present invention relates to a pharmaceutical composition in a solid unit dosage form for oral administration in a human or lower animal comprising:

a. a safe and effective amount of a therapeutically active agent;

b. an inner coating layer selected from the group consisting of poly(methacrylic acid, methyl methacrylate) 1:2, poly(methacrylic acid, methyl methacrylate) 1:1, and mixtures thereof; and c. an outer coating layer comprising an enteric polymer or film coating material; wherein the inner coating layer is not the same as the outer coating layer; wherein if the inner coating layer is poly(methacrylic acid, methyl methacrylate) 1:1 then the outer coating layer is not poly(methacrylic acid, methyl methacrylate) 1:2 or is not a mixture of poly(methacrylic acid, methyl methacrylate) 1:1 and poly(methacrylic acid, methyl methacrylate) 1:2; and wherein the inner coating layer and the outer coating layer contain no therapeutically active agent.

In another embodiment the present invention relates to a pharmaceutical composition in a solid unit dosage form for oral administration in a human or lower animal comprising:

a. a safe and effective amount of a therapeutically active agent;

b. an inner coating layer comprising poly(methacrylic acid, methyl methacrylate) 1:2; and c. an outer coating layer comprising an enteric polymer or film coating material; wherein the inner coating layer is not the same as the outer layer coating. This invention further relates to a method of maintaining the desired site of delivery of a therapeutic agent in the gastrointestinal tract by reducing the impact of coating fractures, through administering the above compositions to a human or lower animal.

DETAILED DESCRIPTION OF THE INVENTION

The phrase "safe and effective amount", as used herein, means an amount of therapeutically active agent or other component of the present compositions, high enough to provide a significant positive modification of the condition to be treated, but low enough to avoid serious side effects (at a reasonable benefit/risk ratio), within the scope of sound medical judgment. A safe and effective amount of therapeutically active agent or other component of the present compositions, will vary with the particular condition being treated, the age and physical condition of the patient being treated, the severity of the condition, the duration of the treatment, the nature of concurrent therapy, the agent selected and like factors.

Therapeutically Active Agent

The methods and compositions of the present invention comprise a safe and effective amount of the therapeutically active agent. In one embodiment the therapeutic agents suitable for incorporation into dosage forms of the present invention are those for which treatment of the colon is therapeutically advantageous. These include therapeutic agents useful for the treatment of diseases of the colon such as constipation, diarrhea, irritable bowel syndrome (IBS), Crohn's disease, colitis, ulcerative colitis, carcinomas, idiopathic protitis, infection in which systemic absorption of the therapeutic agent is neither required or desired, and other diseases or disorders of the colon or rectum. These include actives for constipation and laxatives such as picosulfate and sennasides, anti-diarrheals such as loperamide, nonsteroidal anti-inflammatory drugs such as salicylates, indomethacin, ibuprofen, flurbiprofen, naproxen, piroxicam 5-amino salicylic acid (or pharmaceutically acceptable salts or esters thereof), balsalazide as well as agents disclosed in U.S. Pat. No. 4,412,992, Chan, issued Nov. 1, 1983, as well as NSAIDS disclosed in U.S. Pat. No. 4,552,899, Sunshine et al., issued Nov. 12, 1985, steriods such as hydrocortisone, prednisone, prednisolone, prednisolone phosphate, prednisolone metasulpho-benzoate sodium, prednisolone sodium phosphate, beclomethasone dipropionate and beclomethasone valerate, glucocorticoids such as dextramethazone, antimicrobials or antiparasitic agents, (especially those effective against anaerobic microbes such as methotrexate), 5-aminosalicylic compounds, 4-aminosalicylic compounds, sulfasalazine, benzalazine, erythromycin, chloroguine, iodochlorhydroxyquin, disodohydroxyquin, neomycin and tetracyclines, immunosupressants such as cyclosporine A, chemotherapeutics for treatment of carcinomas, gastointestinal stimulants and prokinetic agents such as cisapride, peppermint oil and other carminative essential oils, actives for the removal of excess bile acids such as cholestyramine. The above references are herein incorporated by reference in their entirety.

Certain therapeutic agents, particularly peptides and proteins, are subject to lumenal degradation in the stomach and small intestine. The colon may be a preferable site of absorption for such compounds since lumenal enzymatic activity is less in the colon (M. Mackay and E. Tomlinson, in Colonic Drug Absorption and Metabolism, P. R. Bieck, ed., Marcel Dekker, Inc., New York, Basel, Hong Kong, 137–158 (1993)). Peptides and proteins that may exhibit improved systemic bioavailability benefit when released in the colon include calcitonin, insulin, and human growth hormone. In certain cases, the peptide or protein may be formulated with a system than enhances the absorption of the macromolecule (M. Mackay and E. Tomlinson, in Colonic Drug Absorption and Metabolism, P. R. Bieck, ed., Marcel Dekker, Inc., New York, Basel, Hong Kong, 137–158 (1993)).

The therapeutically active agents are present in the solid dosage forms in suitable unit dosage amounts. These amounts will be known by those skilled in the art. In one embodiment the active agent is 5-amino salicylic acid or pharmaceutically acceptable salts or esters thereof at a dosage range of from about 400 mg to about 1.5 grams per tablet, in another embodiment is from about 700 mg to about 900 mg per tablet.

The therapeutically active agent may be incorporated into one of the several substrates described herein in a manner consistent with the physical chemical properties of the drug and its pharmacodynamics, using techniques known to those skilled in the art.

The Inner and Outer Coating Layers

In one embodiment the coating layers of the present invention do not contain any therapeutically active agent of the present invention. In addition, the "coating layers" described herein refer to completely encasing or coating all of the solid unit dosage form (does not include coated microcrystal spheres, coated pellets, coated beads, coated microparticles or particles, or coated granules, of the therapeutically active agent).

Inner Coating Layer

The inner coating layer is selected from the group consisting of poly(methacrylic acid, methyl methacrylate) 1:2, poly(methacrylic acid, methyl methacrylate) 1:1, and mixtures thereof. Generally the inner coating layer is selected based on the preferred delivery site desired and is applied to the core of the unit dosage form to achieve a minimum coating thickness from about 20 µm to about 120 µm. The coating thickness depends on the actual size of the unit dosage form, but in one embodiment the minimum coating thickness of the inner coating layer is from about 20 µm to about 50 µm.

In one embodiment the inner coating layer comprises poly (methacrylic acid, methyl methacrylate) 1:2 (Eudragit® S), or other enteric polymer material which has the same pH release characteristics in aqueous media as Eudragit® S. Eudragit® S, an anionic copolymer derived from methacrylic acid and methyl methacrylate, with a ratio of free carboxyl groups to the ester groups of approximately 1:2, and a mean molecular weight of approximately 135,000, from Rohm Tech. In one embodiment the inner coating layer is any other polymer with the same aqueous pH release charcteristics as Eudragit® S.

Outer Coating Layer

The outer coating layer comprises an enteric polymer or film coating material, wherein the inner coating layer is not the same as the outer coating layer. Generally, if the inner coating layer is poly(methacrylic acid, methyl methacrylate) 1:1 (Eudragit® L) then the outer coating layer is not poly(methacrylic acid, methyl methacrylate) 1:2 (Eudragit(® S) or is not a mixture of poly(methacrylic acid, methyl methacrylate) 1:1 and poly(methacrylic acid, methyl methacrylate) 1:2. The outer coating material can be any coating material that protects the inner coating layer from fractures during handling and that dissolves or is removed in the gastrointestinal tract prior to the inner coating layer. The outer coating layer is either a single coating or multiple coatings of either an enteric polymer material or film coating material. In another embodiment the unit dosage form has a single outer coating layer. In another embodiment the outer coating layer is an anionic copolymer. In one embodiment the outer coating cannot comprise an enteric polymer or mixtures thereof with the same pH of release in aqueous media as Eudragit® S. If the inner coating is poly (methacrylic acid, methyl methacrylate 1:2, then the outer coating layer can only comprise poly(methacrylic acid, methyl methacrylate 1:2 (Eudragit® S) if it is mixed with another enteric polymer or film coating material such that the pH of release, in aqueous media, for the mixture is less than the pH of release (aqueous media) for poly(methacrylic acid, methyl methacrylate 1:2 (Eudragit® S) alone.

In another embodiment the outer coating layer is an enteric polymer material that begins to dissolve in an aqueous media at a pH of less than about 7, in another embodiment at a pH of less than about 6.8. Generally the outer coating layer is applied to the core of the unit dosage form to achieve a minimum thickness of from about 10 µm to about 200 µm, in another embodiment is from about 30 µm to about 150 µm.

In one embodiment the outer coating layer is selected from the group consisting of film coatings, cellulose derivatives, cellulose ethers, methyl cellulose, ethylcellulose, carboxymethylcellulose, carboxymethylethylcellulose, hydroxyethyl cellulose, hydroxypropyl cellulose, hydroxypropyl methylcellulose, low viscosity hydroxypropyl cellulose, low viscosity hydroxypropyl methylcellulose, wax or wax like substance, such as carnauba wax, fatty alcohols, hydrogenated vegetable oils, zein, shellac, sucrose, Arabic gum, polyethylene glycol, polyvinylpyrolidone, gelatin, sodium alginate, dextrin, psyllium husk powder, polymethacrylates, anionic polymethacrylates, poly(methacrylic acid, methyl methacrylate) 1:1, mixtures of poly(methacrylic acid, methyl methacrylate) 1:2 and poly(methacrylic acid, methyl methacrylate) 1:1, cellulose acetate phthalate, cellulose acetate trimelliate, hydroxypropyl methylcellulose phthalate (HPMCP), cellulose propionate phthalate, cellulose acetate maleate, polyvinyl alcohol phthalate, hydroxypropyl methylcellulose acetate succinate (HPMCAS), hydroxypropyl methylcellulose hexahydrophthalate, polyvinyl acetate phthalate, poly(methacrylic acid, ethyl acrylate) 1:1, and compatible mixtures thereof.

In another embodiment the outer coating layer is selected from the group consisting of cellulose derivatives, cellulose ethers, methyl cellulose, ethylcellulose, carboxymethylcellulose, carboxymethylethylcellulose, hydroxyethyl cellulose, hydroxypropyl cellulose, hydroxypropyl methylcellulose, low viscosity hydroxypropyl cellulose, low viscosity hydroxypropyl methylcellulose, fatty alcohols, hydrogenated vegetable oils, zein, shellac, sucrose, Arabic gum, polyethylene glycol, polyvinylpyrolidone, gelatin, sodium alginate, dextrin, psyllium husk powder, polymethacrylates, anionic polymethacrylates, poly(methacrylic acid, methyl methacrylate) 1:1, mixtures of poly(methacrylic acid, methyl methacrylate) 1:2 and poly(methacrylic acid, methyl methacrylate) 1:1, cellulose acetate phthalate, cellulose acetate trimelliate, hydroxypropyl methylcellulose phthalate (HPMCP), cellulose propionate phthalate, cellulose acetate maleate, polyvinyl alcohol phthalate, hydroxypropyl methylcellulose acetate succinate (HPMCAS), hydroxypropyl methylcellulose hexahydrophthalate, polyvinyl acetate phthalate, poly(methacrylic acid, ethyl acrylate) 1:1, and compatible mixtures thereof.

In another embodiment the outer coating layer is selected from the group consisting of anionic polymethaclylates, poly(methacrylic acid, methyl methacrylate) 1:1, mixtures of poly(methacrylic acid, methyl methacrylate) 1:2 and poly(methacrylic acid, methyl methacrylate) 1:1, cellulose acetate phthalate, cellulose acetate trimelliate, hydroxypropyl methylcellulose phthalate (HPMCP), cellulose propionate phthalate, cellulose acetate maleate, polyvinyl alcohol phthalate, hydroxypropyl methylcellulose acetate succinate (HPMCAS), hydroxypropyl methylcellulose hexahydrophthalate, polyvinyl acetate phthalate, poly (methacrylic acid, ethyl acrylate) 1:1, and compatible mixtures thereof.

In another embodiment the outer coating layer is a single layer of a mixture of poly(methacrylic acid, methyl methacrylate) 1:1 (Eudragit® L) and poly(methacrylic acid, methyl methacrylate) 1:2 (Eudragit® S) in a ratio of about 1:10 to about 10:1, preferably about 1:5 to about 1:3 more preferably about 2:3. The coating thickness depends on the actual size of the unit dosage form, but in one embodiment the minimum coating thickness of the outer coating layer is from about 10 $\mu$m to about 50 $\mu$m, in another embodiment is from about 20 $\mu$m to about 40 $\mu$m.

In another embodiment the outer coating layer is a single coating of an enteric polymer that begins to dissolve in aqueous media at a pH between about 5 to about 6.3, in another embodiment at a pH between about 5 to about 6, in even another embodiment at a pH between about 5 to about 5.5.

In one embodiment, the function of the outer coating layer is to prevent or minimize fractures of the inner coating layer during formulation processing, manufacturing, and packaging, and the function of the inner coating layer is to maintain the desired point of release of the therapeutic active agent in the gastrointestinal tract. For example if the inner coating is poly(methacrylic acid, methyl methacrylate) 1:2 (Eudragit® S), the present invention maintains the desired point of release, as described, for example, in U.S. Pat. Nos. 5,541,170 and 5,541,171, Rhodes et al., which are incorporated herein by reference in their entirety.

In one embodiment the total coating thickness (both the inner and outer coating layers together) is from about 5 mg/cm$^2$ to about 40 mg/cm$^2$, in another embodiment is from about 10 mg/cm$^2$ to about 15 mg/cm$^2$.

Specific examples of the outer coating layer follow.

Eudragit® L, is an anionic copolymer derived from methacrylic acid and methyl methacrylate, with a ratio of free carboxyl groups to the ester groups of approximately 1:1, and a mean molecular weight of approximately 135,000, from Rohm Tech;

Eudragit® L 30 D, is an aqueous acrylic resin dispersion, an anionic copolymer derived from methacrylic acid and ethyl acrylate with a ratio of free carboxyl groups to the ester groups of approximately 1:1, and a mean molecular weight of approximately 250,000; (it is supplied as an aqueous dispersion containing 30% w/w of dry lacquer substance);

Eudragit® L 100-55, is an anionic copolymer derived from methacrylic acid and ethyl acrylate, with a ratio of free carboxyl groups to the ester groups of approximately 1:1, and a mean molecular weight greater than about 100,000;

cellulose acetate phthalate or CAP®, available from Eastman Chemical;

cellulose acetate trimelliate, CAT® available from Eastman Chemical;

hydroxypropyl methylcellulose phthalate (USP/NF type 220824) HPMCP 50® and (USP/NF type 200731) HPMCP 55® available from Shin Etsu Chemical;

polyvinyl acetate phthalate, PVAP®, available from Colorcon;

hydroxypropyl methylcellulose acetate succinate, HPMCAS®, available from Shin Etsu Chemical;

hydroxypropylcellulose, Klucel®.

To enhance the elasticity of the coating materials, preferably the coating material of the present invention also comprises a plasticizer. Appropriate plasticizers include polyethylene glycols, propylene glycols, 1,2-propylene glycol, dibutyl phthalate, diethyl phthalate, tributyl citrate, tributyrin, butyl phthalyl butyl glycolate (Santicizer® B-16, from Monsanto, St. Louis, Mo.), triacetin, castor oil and citric acid esters; in another embodiment the plasitcizer is dibutyl phthalate, tributyl citrate, or triethyl citrate. These plasticizers are present in an amount to facilitate the coating process and to obtain an even coating film with enhanced physical stability. Generally the coating material comprises from about 0% to about 50% of a plasticizer, preferably from about 2% to about 25% by weight, more preferably from about 10% to about 20% by weight of the enteric polymer.

In addition, to facilitate the coating process, the coating material may also comprise inert solid particulates. Preferred inert solid particulates include talc and titanium dioxide.

The selections of optional plasticizer, optional inert solid particulate, and levels thereof, coating formulation type (solvent, ammoniated aqueous solution, or aqueous dispersion), and process are based upon the specific enteric polymer or film coatings used and the type of dosage form used according to criteria known to those skilled in the art. The solvent for the coating layers may be organic or aqueous. In one embodiment the coating layer is obtained via the use of an aqueous dispersion of the coating material.

The Dosage Form and Method of Making the Dosage Form

A safe and effective amount of therapeutically active agent is incorporated into a solid unit dosage form. The term "solid unit dosage form" means any dosage form, preferably non-liquid, intended to be swallowed and having a sufficiently defined form to be coated. Solid unit dosage forms may be selected from the group consisting of a hard or soft capsule or a compressed tablet. In one embodiment the solid dosage forms of the present invention are selected from the group consisting of soft gelatin capsules; hard gelatin capsules; and compressed tablets of any size or shape. In one embodiment the unit dosage form of the present invention comprises a unit dosage form from about 550 mg to about 1.5 gram total weight, in another embodiment from about 600 mg to about 1.2 grams total weight, and in even another embodiment from about 750 mg to about 1 gram total weight.

In one embodiment the unit dosage form is a spherical or elliptical soft elastic gelatin capsule. The soft elastic gelatin capsule is filled with therapeutically active agent suspended in a suitable vehicle compatible with the soft gelatin capsule.

In still another embodiment the unit dosage form is a hard capsule (i.e. starch or gelatin hard capsule), for example a starch capsule such as Capill® from Capsulgel (Greenwood, S.C.) in which the length of the long axis of the capsule is less than about 10 mm and not more than about 1.5 times greater than the short axis diameter of the capsule. The capsule may be filled with a solid form of therapeutically active agent as described above, or alternatively with therapeutically active agent dissolved or suspended in a suitable vehicle compatible with the capsule wall.

In another embodiment the unit dosage form is a compressed spherical or elliptical tablet. The tablet is comprised of a solid form of therapeutically active agent and is compressed using conventional equipment and processes.

In addition to the therapeutically active agent the compositions of this invention also generally comprise pharmaceutiacally acceptable excipients. As used herein, "excipient" means one or more compatible solid or liquid filler diluents or encapsulating substances which are suitable for administration to a subject. The term "compatible", as used herein, means that the components of the composition are capable of being commingled with the active agent, and with each other, in a manner such that there is no interaction which would substantially reduce the pharmaceutical efficacy of the composition under ordinary use situations. Pharmaceutically-water; acceptable excipients must, of course, be of sufficiently high purity and sufficiently low toxicity to render them suitable for administration to the subject being treated. Excipients may act to facilitate incorporation of the therapeutically active agent into the dosage form, modify the release of the therapeutically active agent from the dosage form, stabilize the therapeutically active agent, or enhance absorption of the therapeutically active agent. Excipients should be safe for their intended use at the levels employed in the formulation. The formulation of therapeutically active agent and excipients is selected according to criteria well known to those skilled in the art to achieve the desired release rate, stability, absorption, and to facilitate the dosage form manufacture.

Some examples of pharmaceutically-acceptable excipients or components thereof are sugars, such as lactose, glucose, and sucrose; starches, such as cornstarch, potato starch, and sodium starch glycolate at a level of about 1% to about 8% by weight, in another embodiment from about 2% to about 4% by weight; cellulose and its derivatives, such as sodium carboxymethyl cellulose, ethyl cellulose, cellulose acetate; powdered tragacanth; malt; gelatin; talc; solid lubricants, such as stearic acid, magnesium stearate; or calcium sulfate; vegetable oils, such as peanut oil, cottonseed oil, sesame oil, olive oil, corn oil, and oil of theobroma; polyols such as propylene glycol, glycerin, sorbitol, mannitol, and polyethylene glycol; alginic acid; emulsifiers, such as the Tweens®; wefting agents such as sodium lauryl sulfate; coloring agents; flavoring agents; excipients; tableting agents; stabilizers; antioxidants; preservatives; pyrogen-free water; isotonic saline; and phosphate buffer solutions. Excipients are described in *Remington's Pharmaceutical Sciences*, Mack Publishing Co. (19th edit. 1995); *Modern Pharmaceutics*, Vol. 7, Chapters 9 & 10, Banker & Rhodes (1979); Lieberman, et al, *Pharmaceutical Dosage Forms: Tablets* (1981); and Ansel, *Introduction to Pharmaceutical Dosage Forms*, 2d (1976). Their selection will depend on secondary considerations like taste, cost, and shelf stability, etc. which are not critical for the purposes of the subject invention, and can be made without difficulty by those skilled in the art.

In one embodiment all of the dosage forms of the present invention are uniform in size prior to coating with the coating layers. The uniform size allows for uniform coating thickness and more uniform dissolution of the coating layers.

Enteric polymers are generally applied onto the unit dosage forms as solutions in organic or aqueous solvents. The solvents commonly employed as vehicles are water, methylene chloride, ethanol, methanol, isopropyl alcohol, acetone, ethyl acetate and combinations thereof. The choice of the solvent is based primarily on the solubility of the polymer, ease of evaporation, and viscosity of the solution.

Some polymers are also available as aqueous systems. These include Eudragit® L30D (methacrylic acid-ethyl acrylate ester copolymer marketed by Rohm-Haas GmBH, West Germany); Aquateric® (cellulose acetate phthalate-containing product marketed by FMC Corporation, Philadelphia, Pa.); and Coateric® (a polyvinyl acetate phthalate based product marketed by Colorcon, Inc., West Point, Pa.). Unlike organic solutions, these aqueous-based systems can be prepared at high concentration without encountering high viscosity. Also, these aqueous systems do not have the problems associated with the organic systems such as flammability, toxicity of the residual solvent in the dosage form, etc.

Coating can be achieved by methods known to one skilled in the art such as by using fluidized bed equipment, perforated pans, a regular pharmaceutical pan, compression coating, continuous or short spray methods, or by drenching. For example, a plasticized dispersion of coating polymer may be applied onto the tablet core comprising the therapeutic active agent by spraying using any suitable spray equipment known in the art. In one embodiment the solid unit dosage forms are coated by continuous spray methods. In one embodiment the outer coating layer is applied after the inner coating layer but before the inner coating layer is dried and/or cured. In yet another embodiment the outer coating layer is applied immediately, e.g. within seconds, after the inner coating layer is applied. If a shiny finish coat is desired on the solid dosage forms of the present invention, a small quantity of polyethylene glycol can be applied to the finished dosage form.

The following non-limiting examples provide typical formulations for compositions of the present invention.

EXAMPLE 1

A wet granulation of 5-ASA (active ingredient), lactose, and povidone is blended with talc, magnesium stearate, sodium starch glycolate, and colloidal silicon dioxide. The blend is compressed into approximately 1034 mg tablets containing 800 mg of the active ingredient on a standard pharmaceutical rotary tablet press.

An inner layer of an EUDRAGIT® S coating of 9.2 mg/cm$^2$ dried coating (i.e. about 62 microns) is applied to the core tablets first by pouring a portion of the coating formula without pigments and then by spraying coating onto the tablets. The coating suspension sprayed onto the tablets contains approximately 62% by weight on a dry basis of Eudragit® S and is based in isopropyl alcohol and acetone with dibutylphthalate as the acting plasticizer.

An outer coating is either applied immediately following the application of the inner coating or once the inner coating has cured. The outer coating layer is sprayed onto the tablets to achieve of 4.1 mg/cm$^2$ dried coating (i.e. about 28 microns). This coating suspension contains approximately 61% by weight on a dry basis of EUDRAGIT® S and L in a ratio of 3:2. It is based in isopropyl alcohol and acetone with dibutylphthalate as the acting plasticizer.

EXAMPLE 2

A wet granulation of 5-ASA (active ingredient), lactose, and povidone is blended with talc, magnesium stearate, sodium starch glycolate, and colloidal silicon dioxide. The blend is compressed into approximately 1570 mg tablets containing 1200 mg of the active ingredient on a standard pharmaceutical rotary tablet press.

An inner layer of an EUDRAGIT® S and L mixture of 8.8 mg/cm$^2$ dried coating (i.e. about 60 microns) is applied to the core tablets first by pouring a portion of the coating formula without pigments and then by spraying coating onto the tablets. The coating suspension sprayed onto the tablets contains approximately 61% by weight on a dry basis of Eudragit® S and L in a ratio of 3:2 and is based in isopropyl alcohol and acetone with dibutylphthalate as the acting plasticizer.

An outer coating is applied immediately following the application of the inner coating or once the inner coating has cured. The outer coating layer is sprayed onto the tablets to achieve of 11.9 mg/cm$^2$ dried coating (i.e. about 80 microns). This coating suspension contains approximately 38% by weight on a dry basis of EUDRAGIT® L and is based in isopropyl alcohol and acetone with triethyl citrate as the acting plasticizer.

EXAMPLE 3

A wet granulation of 5-ASA (active ingredient), lactose, and povidone is blended with talc, magnesium stearate, sodium starch glycolate, and colloidal silicon dioxide. The blend is compressed into approximately 690 mg tablets containing 500 mg of the active ingredient on a standard pharmaceutical rotary tablet press.

An inner layer of an EUDRAGIT® S coating of 15.6 mg/cm$^2$ dried coating (i.e. about 105 microns) is applied to the core tablets first by pouring a portion of the coating formula without pigments and then by spraying coating onto the tablets. The coating suspension sprayed onto the tablets contains approximately 62% by weight on a dry basis of Eudragit® S and is based in isopropyl alcohol and acetone with dibutylphthalate as the acting plasticizer.

An outer coating is applied immediately following the application of the inner coating or once the inner coating has cured. The outer coating layer is a hydroxpropyl methylcellulose coating applied to a thickness of about 100 microns of dried coating according to the following formula:

| Component | Weight per Tablet |
| --- | --- |
| Dri-Klear[1] | 3.7 g |
| White Chroma-Tone[2] | 1 g |
| Water | 48 g |

[1]Dri-Klear is a mixture of hydroxypropyl methylcellulose, polyethylene glycol, hydroxypropyl cellulose, and silicon dioxide, manufactured by CHR Hansen.
[2]White Chroma-Tone is a mixture of titanium dioxide and hydroxypropyl methylcellulose, manufactured by CHR Hansen.

EXAMPLE 4

Core tablets are manufactured to the following formula:

| Component | Weight per Tablet |
| --- | --- |
| Ketoprofen | 2 mg |
| Lactose | 4.96 mg |
| Starch | 0.80 mg |
| polyvinylpyrrolidone (PVP) | 0.16 mg |
| Magnesium stearate | 0.8 mg |

An inner layer of an EUDRAGIT® S coating about 20 microns is applied to the core tablets by spraying coating of the following formula:

| Component | | |
| --- | --- | --- |
| EUDRAGIT ® S100 | | 3 g |
| Diethyl phthalate | | 0.75 ml |
| Silicone fluid 200/20CS | | 0.75 ml |
| Methanol | 25 parts | 100 ml |
| Dichloromethane | 75 parts | |

An outer coating layer is applied to the core tablet and inner coating layer. The outer coating layer is a hydroxypropyl methylcellulose coating applied to a thickness of about 150 microns of dried coating according to the following formula:

| Component | |
| --- | --- |
| Dri-Klear[3] | 3.7 g |
| White Chroma-Tone[4] | 1 g |
| Water | 48 g |

[3]Dri-Klear is a mixture of hydroxypropyl methylcellulose, polyethylene glycol, hydroxypropyl cellulose, and silicon dioxide, manufactured by CHR Hansen.
[4]White Chroma-Tone is a mixture of titanium dioxide and hydroxypropyl methylcellulose, manufactured by CHR Hansen.

EXAMPLE 5

Applied to the core tablets described in Example 4 is an inner layer of an aqueous EUDRAGIT® L 30 D-55 coating of about 70 microns dried coating of the following formula:

| Component | |
|---|---|
| EUDRAGIT® L 30 D-55 | 260 g |
| Talc | 39 g |
| Polyethylene glycol 6000 | 16 g |
| Water | 345 g |

An outer coating layer is then applied as a hydroxypropyl methylcellulose coating to a thickness of about 50 microns of dried coating according to the following formula:

| Component | |
|---|---|
| Dri-Klear[5] | 3.7 g |
| White Chroma-Tone[6] | 1 g |
| Water | 48 g |

[5]Dri-Klear is a mixture of hydroxypropyl methylcellulose, polyethylene glycol, hydroxypropyl cellulose, and silicon dioxide, manufactured by CHR Hansen.
[6]White Chroma-Tone is a mixture of titanium dioxide and hydroxypropyl methylcellulose, manufactured by CHR Hansen.

EXAMPLE 6

The following formulation is encapsulated within soft or hard gelatin capsules:

| Component | Weight per Tablet |
|---|---|
| Insulin | 20 i.u. (c.a. 1 mg) |
| Sodium 5-methoxy salicyclate | 150.0 mg |
| PEG 4000 | 3.5 mg |
| PEG 600 | 187.5 mg |
| Capsule fill wt | 342 mg |

Thereafter, the capsule is coated. An inner layer of an EUDRAGIT® S coating is applied to the capsules by spraying coating of the following formula to a thickness of about 100 microns dried coating:

| Component | |
|---|---|
| EUDRAGIT® S100 | 70 g |
| Triethyl citrate | 14 g |
| Acetone | 283 g |
| Isopropyl Alcohol | 483 g |

Following the application of the inner coating, an outer coating layer of an EUDRAGIT® S and L mixture at a ratio of 2:3 of about 20 microns is applied to the tablets by spraying a coating of the following formula:

| Component | Weight per Tablet |
|---|---|
| EUDRAGIT® L100 | 42 g |
| EUDRAGIT® S100 | 28 g |
| Triethyl citrate | 14 g |
| Acetone | 283 g |
| Isopropyl Alcohol | 483 g |

While particular embodiments of the present invention have been described, it will be obvious to those skilled in the art that various changes and modifications of the present invention can be made without departing from the spirit and scope of the invention. It is intended to cover, in the appended claims, all such modifications that are within the scope of this invention.

What is claimed is:

1. A pharmaceutical composition in a solid unit dosage form for oral administration in a human or lower animal consisting essentially of:
   a. a safe and effective amount of a therapeutically active agent;
   b. an inner coating layer selected from the group consisting of poly(methiacrylic acid, methyl methacrylate) 1:2, poly(methacrylic acid, methyl methacrylate) 1:1, and mixtures thereof; and
   c. an outer coating layer, applied to the inner coating layer, said outer coating layer comprising an enteric polymer that begins to dissolve in an aqueous medium at a pH of less than about 7, said enteric polymer being selected from the group consisting of polymethacrylates, anionic polymethacrylates, poly(methacrylic acid, methyl methacrylate) 1:1, mixtures of poly(methacrylic acid, methyl methacrylate) 1:2 and poly(methacrylic acid, methyl methacrylate) 1;1, polyvinyl acetate phthalate, poly(methacrylic acid, ethyl acrylate) 1:1, and compatible mixtures thereof;
   wherein the inner coating layer is not the same as the outer coating layer;
   wherein if the inner coating layer is poly(methacrylic acid, methyl methacrylate) 1:1 then the outer coating layer is not poly(methacrylic acid, methyl methacrylate) 1:2 or is not a mixture of poly(methacrylic acid, methyl methacrylate) 1:1 and poly(methacrylic acid, methyl methacrylate) 1:2; and
   wherein the inner coating layer and the outer coating layer contain no therapeutically active agent.

2. The composition of claim 1 wherein the inner coating layer is poly(methacrylic acid, methyl methacrylate) 1:2.

3. The composition of claim 1 wherein the outer coating layer is selected from the group consisting of poly(methacrylic acid, methyl methacrylate) 1:1, and mixtures of poly(methacrylic acid, methyl methacrylate) 1:2 and poly(methacrylic acid, methyl methacrylate) 1:1.

4. The composition of claim 3 wherein the outer coating layer is a mixture of poly(methacrylic acid, methyl methacrylate) 1:2 and poly(methacrylic acid, methyl methacrylate) 1:1.

5. The composition of claim 1 wherein the total coating thickness of the inner and outer coating layers combined is from about 5 mg/cm$^2$ to about 40 mg/cm$^2$.

6. The composition of claim 5 wherein the total coating thickness is from about 10 mg/cm$^2$ to about 15 mg/cm$^2$.

7. The composition of claim 6 wherein the solid dosage form is coated by continuous spray methods wherein the outer coating layer is applied after the inner coating layer but before the inner coating layer is dried or cured.

8. The composition of claim 1 wherein the therapeutically active agent is selected from the group consisting of laxatives, anti-diarrheals, nonsteroidal anti-inflammatory agents, 5-amino salicylic acid, glucocorticoids, antimicrobials, immunosuppressants, chemotherapeutics or anti-cancer drugs, peptides, proteins, cardiovascular drugs, psychotropic drugs, H2-blockers, antiasthmatic agents, and antihistamines.

9. The composition of claim 8 wherein the therapeutically active agent is a nonsteroidal anti-inflammatory agent.

10. The composition of claim 9 wherein the therapeutically active agent is 5-amino salicylic acid.

11. A pharmaceutical composition in a solid unit dosage form for oral admininstration in a human or lower animal consisting essentially of:
   a. a safe and effective amount of a therapeutically active agent;
   b. an inner coating layer comprising poly(methacrylic acid, methyl methacrylate) 1:2; and
   c. an outer coating layer, applied to the inner coating layer, said outer coating layer comprising an enteric polymer that begins to dissolve in an aqueous medium at a pH of less than about 7, said enteric polymer being selected from the group consisting of polymethacrylates, anionic polymethacrylates, poly(methacrylic acid, methyl methacrylate) 1:1, mixtures of poly(methacrylic acid, methyl methacrylate) 1:2 and poly(methacrylic acid, methyl methacrylate) 1:1, polyvinyl acetate phthalate, poly(methacrylic acid, ethyl acrylate) 1:1, and compatible mixtures thereof;
   wherein the inner coating layer is not the same as the outer coating layer.

12. The composition of claim 11 wherein the outer coating layer is selected from the group consisting of poly (methacrylic acid, methyl methacrylate) 1:1 and mixtures of poly(methacrylic acid, methyl methacrylate) 1:2 and poly (methacrylic acid, methyl methacrylate) 1:1.

13. The composition of claim 12 wherein the outer coating layer is a mixture of poly(methacrylic acid, methyl methacrylate) 1:2 and poly(methacrylic acid, methyl methacrylate) 1:1.

14. The composition of claim 11 wherein the total coating thickness of the inner and outer coating layers combined is from about 5 mg/cm² to about 40 mg/cm².

15. The composition of claim 14 wherein the total coating thickness is from about 10 mg/cm² to about 15 mg/cm².

16. The composition of claim 15 wherein the solid dosage form is coated by continuous spray methods wherein the outer coating layer is applied after the inner coating layer but before the inner coating layer is dried or cured.

17. The composition of claim 11 wherein the therapeutically active agent is selected from the group consisting of laxatives, anti-diarrheals, nonsteroidal anti-inflammatory agents, 5-amino salicylic acid, glucocorticoids, antimicrobial, immunosuppressants, chemotherapeutics or anti-cancer drugs, peptides, proteins, cardiovascular drugs, psychotropic drugs, H2-blockers, antiasthmatic agents, and antihistamines.

18. The composition of claim 17 wherein the therapeutically active agent is a nonsteroidal anti-inflammatory agent.

19. The composition of claim 18 the therapeutically active agent is 5-amino salicylic acid.

20. The composition of claim 11 wherein the solid dosage form is a compressed tablet.

21. A method of consistent and reliable delivery and release of a therapeutically active agent to the desired region of delivery by orally administering the composition of claim 1.

22. A method of consistent and reliable delivery and release of a therapeutically active agent to the desired region of delivery by orally administering the composition of claim 11.

23. The composition of claim 1 wherein the solid dosage form is a compressed tablet.

24. The composition of claim 1 wherein the solid unit dosage form has a total weight from about 600 mg to about 1200 mg.

25. The composition of claim 10 wherein the 5-amino salicylic acid is present in an amount from about 700 mg to about 900 mg per solid unit dosage form.

26. The composition of claim 1 wherein the outer coating layer has a minimum thickness from about 10 µm to about 200 µm.

27. The composition of claim 4 wherein the outer coating layer has a minimum thickness from about 10 µm to about 50 µm.

28. The composition of claim 27 wherein the outer coating layer has a minimum thickness from about 20 µm to about 40 µm.

29. The composition of claim 11 wherein the solid unit dosage form has a total weight from about 600 mg to about 1200 mg.

30. The composition of claim 19 wherein the 5-amino salicylic acid is present in an amount from about 700 mg to about 900 mg per solid unit dosage form.

31. The composition of claim 11 wherein the outer coating layer has a minimum thickness from about 10 µm to about 200 µm.

32. The composition of claim 13 wherein the outer coating layer has a minimum thickness from about 10 µm to about 50 µm.

33. The composition of claim 32 wherein the outer coating layer has a minimum thickness from about 20 µm to about 40 µm.

34. A pharmaceutical composition in a solid unit dosage form for oral administration in a human or lower animal consisting essentially of:
   a. a safe and effective amount of 5-amino salicylic acid;
   b. an inner coating layer comprising poly(methacrylic acid, methyl methacrylate) 1:2; and
   c. an outer coating layer, applied to the inner coating layer, said outer coating layer comprising an enteric polymer that begins to dissolve in an aqueous medium at a pH of less than about 7, said enteric polymer being a mixture of poly(methiacrylic acid, methyl methacrylate) 1:2 and poly(methacrylic acid, methyl methacrylate) 1:1.

35. A method of consistent and reliable delivery and release of 5-amino salicylic acid to the desired region of delivery by orally administering the composition of claim 34.

* * * * *

UNITED STATES PATENT AND TRADEMARK OFFICE
CERTIFICATE OF CORRECTION

PATENT NO. : 6,893,662 B2
DATED : November 15, 2001
INVENTOR(S) : Gregory Paul Dittmar et al.

It is certified that error appears in the above-identified patent and that said Letters Patent is hereby corrected as shown below:

Column 5,
Line 44, delete "polymethaclylates" and insert -- polymethacrylate --.

Column 7,
Line 56, delete "water;".

Column 8,
Line 16, delete "wefting" and insert -- wetting --.

Column 12,
Line 23, delete "poly(methiacrylic" and insert -- poly(methacrylic --.

Column 13,
Line 56, delete "antimicrobial" and insert -- antimicrobials --.
Line 62, insert the word -- wherein -- after "claim 18.".

Column 14,
Line 55, delete "methiacrylic" and insert -- methacrylic --.

Signed and Sealed this

Sixth Day of December, 2005

JON W. DUDAS
*Director of the United States Patent and Trademark Office*